United States Patent [19]

Aumueller et al.

[11] Patent Number: 4,981,969
[45] Date of Patent: Jan. 1, 1991

[54] POLYALKYLPIPERIDINE-SUBSTITUTED TETRAHYDROPYRIDONES AND USE THEREOF

[75] Inventors: Alexander Aumueller, Deidesheim; Peter Neumann, Mannheim; Hubert Trauth, Dudenhofen, all of Fed. Rep. of Germany

[73] Assignee: BASF Aktiengesellschaft, Ludwigshafen, Fed. Rep. of Germany

[21] Appl. No.: 443,478

[22] Filed: Nov. 30, 1989

[30] Foreign Application Priority Data

Dec. 30, 1988 [DE] Fed. Rep. of Germany ....... 3844355

[51] Int. Cl.⁵ .......................................... C07D 401/14
[52] U.S. Cl. .................................... 546/187; 546/190
[58] Field of Search ................................ 546/187, 190

[56] References Cited

U.S. PATENT DOCUMENTS

| | | | |
|---|---|---|---|
| 4,238,613 | 12/1980 | Rasberger et al. | 546/190 |
| 4,279,804 | 7/1981 | Cantatore et al. | 546/187 |
| 4,762,872 | 8/1988 | Lai et al. | 546/190 |
| 4,769,457 | 9/1988 | Helwig et al. | 544/180 |

*Primary Examiner*—Richard L. Raymond
*Assistant Examiner*—Ba K. Trinh
*Attorney, Agent, or Firm*—Oblon, Spivak, McClelland, Maier & Neustadt

[57] ABSTRACT

Tetrahydropyridones which in one of their tautomeric forms conform to the general formula (I)

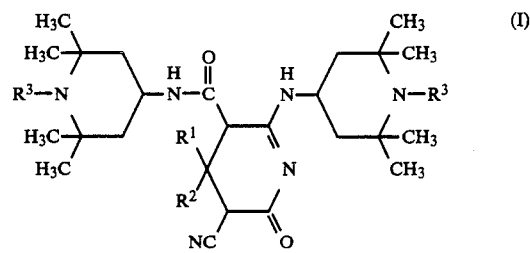

where
$R^1$ and $R^2$ are each independently of the other $C_1-C_{12}$-alkyl, which may be oxygen-interrupted, $C_5-C_6$-cycloalkyl or $C_7-C_{12}$-phenylalkyl where the phenyl is unsubstituted or monosubstituted, disubstituted or trisubstitued by $C_1-C_4$-alkyl, $C_1-C_4$-alkoxy, fluorine, chlorine or bromine, or

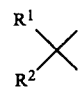

is a from 5- to 12-membered cycloaliphatic ring which may be monosubstituted, disubstituted, trisubstituted or tetrasubstituted by $C_1-C_4$-alkyl, and
$R^3$ is hydrogen, substituted or unsubstituted alkyl or phenyl alkyl or alkanoyl, are effective stabilizers for plastics and coatings.

6 Claims, No Drawings

POLYALKYLPIPERIDINE-SUBSTITUTED TETRAHYDROPYRIDONES AND USE THEREOF

It is known that polyalkylpiperidine derivatives protect organic polymers from destruction by light and heat.

Unsatisfactory aspects of prior art compounds are frequently the low compatibility with polyolefins and other plastics, the insufficient duration of the protective effect, the self-color of the substances, and their volatility and proneness to thermal decomposition on incorporation at elevated temperature.

It is an object of the present invention to provide new stabilizers which are free of the aforementioned disadvantages.

We have found that this object is achieved by the novel heterocycles of the formula (I).

The present invention accordingly provides polyalkylpiperidine-substituted tetrahydropyridones which in one of their tautomeric forms conform to the general formula (I)

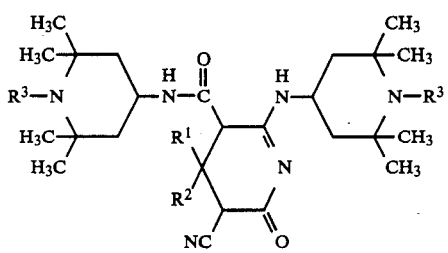

where
$R^1$ and $R^2$ are each independently of the other $C_1$–$C_{12}$-alkyl, which may be oxygen-interrupted, $C_5C_8$-cycloalkyl or $C_7$–$C_{12}$-phenylalkyl where the phenyl is unsubstituted or monosubstituted, disubstituted or trisubstituted by $C_1$–$C_4$-alkyl, $C_1$–$C_4$-alkoxy, fluorine, chlorine or bromine, or

is a from 5- to 12-membered cycloaliphatic ring which may be monosubstituted, disubstituted, trisubstituted or tetrasubstituted by $C_1$–$C_4$-alkyl, and
$R^3$ is hydrogen, $C_1$–$C_8$-alkyl, $C_2$–$C_3$-cyanoalkyl, $C_2$–$C_4$-hydroxyalkyl, $C_2$–$C_{10}$-phenylalkyl where the phenyl is unsubstituted or monosubstituted or disubstituted by $C_1$–$C_4$-alkyl, $C_1$–$C_4$-alkoxy, fluorine, chlorine or bromine,
and acid addition salts and hydrates thereof Alkyl $R^3$ can be linear or branched Specific examples are: ethyl, propyl, n-butyl, n-pentyl, isopentyl, n-hexyl, n-heptyl and n-octyl Preferred alkyl $R^3$ is methyl.

Suitable alkanoyl $R^3$ is propionyl, butanoyl, pentanoyl, hexanoyl, heptanoyl, octanoyl, benzoyl or in particular acetyl.

Phenylalkyl $R^3$ is for example phenylethyl or preferably benzyl.

Phenylalkyl with substitution on the phenyl is for example 3- or 4-methoxybenzyl, 3- or 4-methoxyphenylethyl, 3- or 4-chlorobenz-yl, 3- or 4-chlorophenylethyl, 3- or 4-ethoxybenzyl, 3- or 4-ethoxyphenylethyl and 3- or 4-methylbenzyl, of which 3-methylbenzyl and 4-methylbenzyl are preferred.

Cyanoalkyl $R^3$ is for example cyanoethyl or in particular cyanomethyl.

Hydroxyalkyl $R^3$ is for example 3-hydroxypropyl, 4-hydroxybutyl- or preferably 2-hydroxyethyl. Aminoalkyl $R^3$ is for example 3-aminopropyl or preferably 2-aminoethyl. Particularly preferred $R^3$ is hydrogen.

$C_1$–$C_{12}$-Alkyl $R^1$ or $R^2$ may be branched or linear. Examples thereof are: methyl, ethyl, propyl, butyl, pentyl, hexyl, isopropyl, isobutyl, isopentyl, tertiary butyl, tertiary amyl, heptyl, n-octyl, i-octyl, nonyl, decyl, undecyl and dodecyl.

Phenylalkyl $R^1$ or $R^2$ has from 7 to 12 carbon atoms and no substituents or from 1 to 3 $C_1$–$C_4$-alkyl, $C_1$–$C_4$-alkoxy, fluorine, chlorine or bromine substituents on the phenyl. Examples here are benzyl, phenylethyl, phenylpropyl, phenylbuty-1, 3- or 4-methoxy-benzyl, 3- or 4- 0 methoxyphenylethyl, 3- or 4-chlorobenz-yl, 3- or 4-chlorophenylethyl, 3- or 4-ethoxyb-enzyl, 3- or 4-ethoxyphenyl ethyl, 3- or 4-methylbenzyl and 3- or 4-ethylbenzyl.

Cycloalkyl $R^1$ or $R^2$ is for example cyclopentyl or cyclohexyl.

can also be a from 5- to 12-membered cycloaliphatic ring which may be substituted by from 1 to 4 $C_1$–$C_4$-alkyl groups.

Examples thereof are cyclopentyl, cyclohexyl, 4methylcyclohexyl,3,3,5,5-tetramethylcyclohexyl,4-tert-butylcyclohexyl, cycloheptyl, cyclooctyl and cyclododecyl.

Preferably, $R^1$ and $R^2$ are each $C_1$–$C_5$-alkyl which may be linear or branched Preference is further given to compounds where

is cyclopentyl, cyclohexyl, cycloheptyl or cyclodo decyl.

The compounds (I) can be prepared by reactinq ketones of the general formula (II) with cyanoacetamides of the general formula (III) in a solvent in the presence of a basic catalyst.

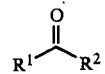

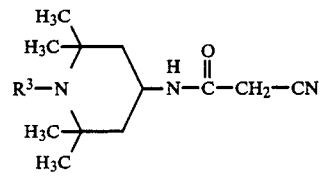

Suitable solvents are organic solvents but also water. Suitable organic solvents are for example alcohols and aromatics such as toluene and xylene.

Suitable alcohol solvents are ethanol, n-propanol, isopropanol, n-butanol and in particular methanol.

The preferred solvents are methanol and water.

Suitable basic catalysts are for example amines, alcoholates and alkali metal hydroxides Suitable amines are for example triethylamine, tributylamine, morpholine, pyridine, quinoline and in particular piperidine.

Suitable alcoholates are for example the alkali metal salts of $C_1$–$C_4$-alcohols, such as sodium ethoxide, potassium tert-butoxide and preferably sodium methoxide.

Suitable alkali metal hydroxides are for example lithium hydroxide, potassium hydroxide and sodium hydroxide. Of these, sodium hydroxide is preferred.

The compounds (I) according to the present invention can be present in the form of the free bases, the hydrates or the salts. Suitable anions come for example from inorganic acids, carboxylic acids and sulfonic acids. Of the salts, those of carboxylic acids and sulfonic acids are preferred.

Suitable inorganic anions are for example chloride, bromide, sulfate, methosulfate, tetrafluoborate, phosphate and thiocyanate.

Sulfonic acid anions are for example benzenesulfonate and tosylate.

Suitable carboxylic acid anions are for example formate, acetate, propionate, hexanoate, cyclohexanoate, lactate, stearate, dodecylbenzoate, benzoate, acrylate, methacrylate, citrate, malonate, succinate and anions of polycarboxylic acids having up to about 3000 COOH groups.

The present invention also relates to the use of (I) as stabilizers for plastics and coatings.

The compounds (I) according to the present invention can be mixed with the plastics in any known apparatus by any method for mixing stabilizers or other additives into polymers.

The plastics stabilized with the compounds according to the present invention may contain further additives, for example antioxidants, light stabilizers, metal deactivators, antistats, flame retardants, pigments and/or fillers.

Antioxidants and light stabilizers which may be added to the plastics as well as the compounds according to the present invention are for example compounds based on sterically hindered phenols or sulfur- or phosphorus-containing costabilizers.

Such phenolic antioxidants are for example 2,6-di-tert.-butyl-4-methylphenol, n-octadecyl β-(3,5-di-tert.-butyl-4-hydroxyphenyl)propionate, 1,1,3-tris(2-methyl-4-hydroxy-5-tert.-butylphenyl)butane, 1,3,5-trimethyl-2,4,6-tris(3,5-di-tert.-butyl-4-hydroxybenzyl) 1,3,5-tris(3,5-di-tert.-butyl-4-hydroxybenzyl) isocyanurate, 1,3,5-tris[β-(3,5-di-tert -butyl-4-hydroxy-phenyl)propionyloxyethyl]isocyanurate, 1,3,5tris(2,6-dimethyl-3-hydroxy-4-tert.-butylbenzyl) isocyanurate and pentaerythritol tetrakis[β-(3,5-di-tert.-butyl-4-hydroxyphenyl)propionate].

Suitable phosphorus-containing antioxidants are for example tris(nonylphenyl) phosphite, distearyl pentaerythritol diphosphite, tris(2,4-di-tert.-butylphenyl) phosphite, tris(2-tert.-butyl-4-methylphenyl) phosphite, bis(2,4-di-tert.-but-Ylphenyl) pentaerythritol diphosphite and tetrakis(2,4-di-tert.-butylphenyl) 4,4,-biphenylene diphosphite.

Suitable sulfur-containing antioxidants are for example dilauryl thiodipropionate, dimyristyl thiodipropionate, distearyl thiodipropionate, pentaerythritol tetrakis(β-laurylthiopropionate) and pentaerythritol tetrakis(β-hexylthiopropionate).

Further antioxidants and light stabilizers which may be used together with the compounds according to the present invention are for example 2-(2'-hydroxyphenyl)-benzotriazoles, 2-hydroxybenzophenones, aryl esters of hydroxybenzoic acids, α-cyanocinnamic acid derivatives, nickel compounds, oxalodianilides or benzimidazolecarboxanilides.

Suitable organic plastics for stabilization by the compounds according to the present invention are for example: polymers of mono- and diolefins, eg. low or high density polyethylene, linear poly-1-butene, polyisoprene, polybutadiene and copolymers of mono- and diolefines or mixtures thereof; copolymers of mono- and diolefines with other vinyl monomers, eg. ethylene/alkyl acrylate copolymers, ethylene/alkyl methacrylate copolymers, ethylene/vinyl acetate copolymers or ethylene/acrylic acid copolymers; polystyrene; copolymers of styrene or α-methylstyrene with dienes or acryloyl derivatives, e.g. styrene-butadiene, styrene-acrylonitrile, styrene/ethyl methacrylate, styrene/-butadiene/ethylacrylate, styrene-acrylonitrile-methacrylate; ABS, MBS or similar polymers; halogen-containing polymers, e.g. pol yvinyl chloride, polyvinyl fluoride, polyvinylidene fluoride and copolymers thereof; polymers derived from α,β-unsaturated acids and derivatives thereof, such as polyacrylates and polymethacrylates, polyacrylamides and polyacrylonitriles; polymers derived from unsaturated alcohols and amines or acryloyl derivatives thereof or acetals, such as polyvinyl alcohol or polyvinyl acetate; polyurethanes, polyamides, polyureas, polyesters, polycarbonates, polysulfones, polyether sulfones and polyether ketones (I) can also be used to stabilize coatings, for example industrial coatings, especially two-coat automotive baking finishes.

Here too it is possible to include the above-mentioned antioxidants and light stabilizers.

The compounds according to the present invention can be added to the coating composition in a solid or dissolved form. Their ready solubility in coating systems is of particular advantage here.

The invention is illustrated in more detail by the Examples which follow. In no case have the conditions of preparation been optimized.

EXAMPLE 1

800 ml of ethanol, 1356 g of ethyl cyanoacetate and 1860 g of 2,2,6,6-tetramethyl-4-aminopiperidine were boiled for 7 hours and then cooled down to 10° C. in an icebath. The resulting precipitate was filtered off with suction and washed with cold ethyl acetate. This gave 1588 g of the compound of the formula

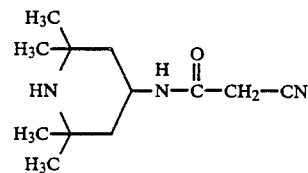

as a colorless solid of melting point 148° C.

EXAMPLE 2

66.9 g of the product of Example 1, 11.6 g of acetone and 5 ml of piperidine were added to 125 ml of water at room temperature. After stirring for 3 hours and standing overnight, the resulting precipitate was filtered off with suction, washed with water and dried at 100° C. under an aspirator vacuum. This gave 66 g of the compound of the formula

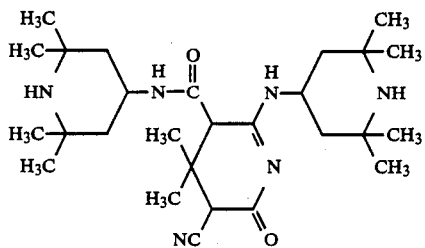

as a colorless hemihydrate of melting point 291° C. (dec.). C$_{27}$H$_{46}$O$_2$N$_6$ . 0.5 H$_2$O (M 495.7)
calculated: C 65.4; H 9.6; N 17.0; O 8.1%
found: C 65.4; H 9.7; N 16.9; O 7.8%

EXAMPLE 3

10.8 g of ethyl methyl ketone were added to 66.9 g of the product of Example 1 and 54 g of 30% strength methanolic sodium methoxide solution in 300 ml of methanol. After standing at room temperature for 48 hours, the solvent was removed under reduced pressure, the residue was dissolved in 250 ml of water, the solution was brought to pH 9.1 with dilute hydrochloric acid, and the resulting precipitate was filtered off with suction, boiled up with acetonitrile and again filtered off with suction. This gave 45 g of hydrochloride of melting point 261° C. (dec.). The hydrochloride was suspended in water, the suspension was brought to pH 13 with NaOH, and the solids were filtered off with suction and dried at 90° C. under reduced pressure. This gave 28 g of the compound of the formula

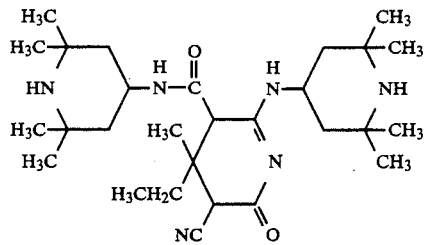

as a colorless solid of melting point 284° C. (dec.).
The compound crystallized with 1.5 moles of water.
C$_{28}$H$_{48}$O$_2$N$_6$ . 1.5 H$_2$O (M 527.8)
calculated: C 63.7; H 9.7; N 15.9; O 10.6%
found: C 63.9; H 9.7; N 15.8; O 9.8%

EXAMPLE 4

66.9 g of the product of Example 1, 54 g of 30% strength methanolic sodium methoxide solution and 15 g of 4-methyl-2-pentanone in 300 ml of methanol were reacted and worked up as in Example 3. Boiling out with ethyl acetate and water gave 16.0 g of the compound of the formula

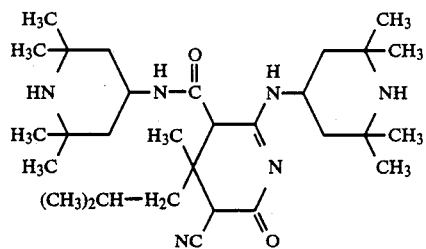

as a colorless hydrate of melting point 268-269° C. (dec.).
C$_{30}$H$_{42}$N$_6$O$_2$ . H$_2$O (M 546.8)
calculated: C 65.9; H 9.9; N 15.4; O 8.8%
found C 66.0; H 9.8; N 15.3; O 8.7%

EXAMPLE 5

66.9 g of the product of Example 1, 54 g of 30% strength methanolic sodium methoxide solution and 29.7 g of di-n-hexyl ketone were left to stand in 300 ml of methanol at room temperature for 2 days. 9 ml of water were then added, the mixture was stirred for 7 hours, and the solvent was then removed under an aspirator vacuum. The residue was suspended in 500 ml of water, the suspension was brought to pH 8.95 with dilute hydrochloric acid, and the solids were filtered off with suction and washed with water. Recrystallization from acetonitrile (addition of active charcoal) left 18 g of the compound of the formula

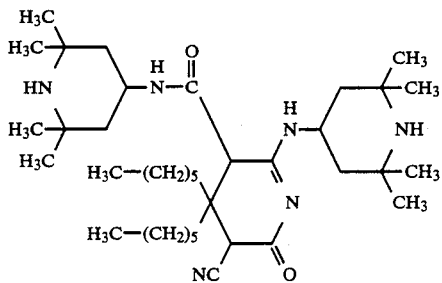

as a colorless solid of melting point 219-220° C. (dec.).
C$_{37}$H$_{66}$N$_6$O$_2$ (M 627.0)
calculated: C 70.9; H 10.6; N 13.4; O 5.1%
found C 70.7; H 10.7; N 13.4; O 5.1%

EXAMPLE 6

66.9 g of the product from Example 1, 54 g of 30% strength methanolic sodium methoxide solution and 12.6 g of cyclopentanone were left to stand in 300 ml of methanol at room temperature for 18 hours. After the solvent had been removed under an aspirator vacuum, 400 ml of water and 500 ml of dichloromethane were added, and the resulting precipitate was filtered off with suction. Recrystallization from acetonitrile left 20 g of the compound of the formula

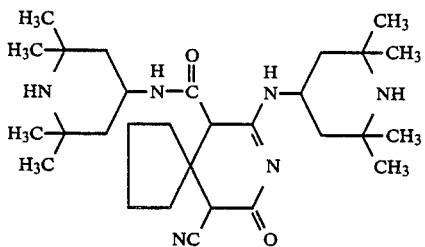

as a colorless solid of melting point 290° C. (dec.).

After drying at 90° C. under an aspirator vacuum the compound contained 1.5 moles of water of crystallization.

C$_{29}$H$_{48}$N$_6$O$_2$ . 1.5 H$_2$O (M 531.8)
calculated: C 64.5; H 9.5; N 15.6; O 10.4%
found: C 64.1; H 9.6 ; N 15.6; O 10.2%

EXAMPLE 7

147.2 g of the product of Example 1, 118 g of 30% strength methanolic sodium methoxide solution and 32.3 g of cyclohexanone in 300 ml of methanol were reacted and worked up as described in Example 6. Boiling up with acetone left 84 g of the compound of the formula

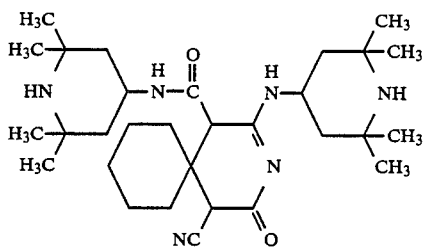

as a colorless hemihydrate of melting point >330° C. (dec.).

C$_{30}$H$_{51}$N$_6$O$_2$ . 0.5 H$_2$O (M 536.8)
calculated: C 67.1; H 9.8; N 15.7; O 7.4%
found: C 67.1; H 9.4; N 15.6; O 7.1%

EXAMPLE 8

66.9 g of the product of Example 1, 54 g of 30% strength methanolic sodium methoxide solution and 16.8 g of cyclopentanone were left to stand in 300 ml of methanol for 6 days. After the solvent had been removed under an aspirator vacuum, the residue was taken up in 500 ml of water, the mixture was brought to pH 9 with dilute hydrochloric acid and filtered off with suction, and the residue was boiled up with water and then with acetonitrile. This left 8.5 g of the compound of the formula

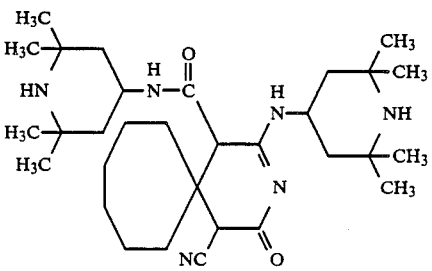

as a colorless hemihydrate of melting point 278° C. (dec.).

C$_{31}$H$_{52}$N$_6$O$_2$ . 0.5 H$_2$O (M 549.8)
calculated: C 67.7; H 9.7; N 15.3; O 7.3%
found C 67.6; H 9.6; N 15.1; O 7.1%

EXAMPLE 9

66.9 g of the product of Example 1, 54 g of 30% strength methanolic sodium methoxide solution and 27.3 g of cyclododecanone were left to stand in 300 ml of methanol for 3 days. After the solvent had been removed under an aspirator vacuum, the residue was taken up in ml of water, the mixture was brought to pH 9 with dilute hydrochloric acid and filtered off with suction, and the residue was washed with water and recrystallized from acetonitrile to give 12 g of the compound of the formula

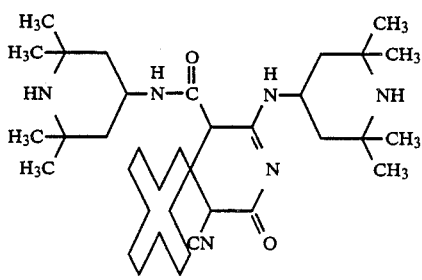

as a colorless hemihydrate of melting point 278° C. (dec.).

C$_{36}$H$_{62}$N$_6$O$_2$ . 0.5 H$_2$O (M 619.9)
calculated: C 69.7; H 10.2; N 13.6; O 6.4%
found: C 69.6; H 10.1; N 13.4; O 6.2

EXAMPLE 10

223 g of the product of Example 1, 58.3 g of methoxyacetone and 12 ml of piperidine were stirred in ml of water for 18 hours. Filtering off with suction and drying left 94 g of the compound of the formula

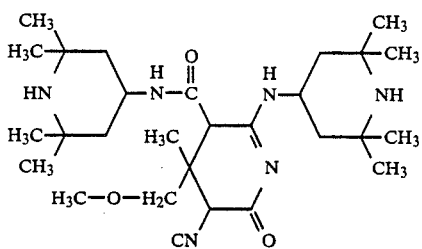

as a colorless hemihydrate of melting point 264° C. (dec.). The product can be further purified by recrystallization from 3:1 acetonitrile/isopropanol.

C$_{28}$H$_{48}$N$_6$O$_3$ . 0.5 H$_2$O (M 525.7)
calculated: C 64.0; H 9.4; N 16.0; O 10.7%
found C 63.6; H 9.4; N 15.9; O 10.7%

EXAMPLE 11

37.9 g of the product of Example 1, 12.4 g of 4-methylcyclohexanone and 1 ml of piperidine were stirred in 50 ml of methanol for 8 hours. The resulting precipitate was filtered off with suction, boiled up with water, filtered off again with suction and dried. This gave 5.7 g of the compound of the formula

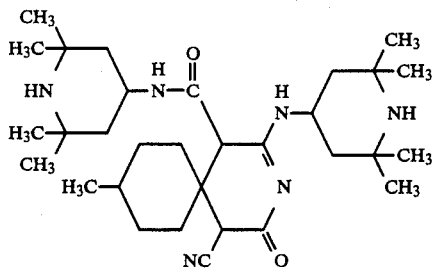

as a colorless solid of melting point 268° C. (dec.), which contained 0.75 mole of water.

$C_{31}H_{52}N_6O_2 \cdot 0.75\ H_2O$ (M 554.3)

calculated: C 67.2; H 9.7; N 15.2; O 7.9%
found: C 67.0; H 9.7; N 14.9; O 7.9%

We claim:

1. A polyalkylpiperidine-substituted tetrahydropyridone which in one of its tautomeric form conforms to the general formula (I)

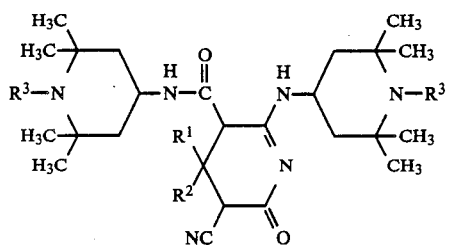

where

R$^1$ and R$^2$ are each independently of the other $C_1$-$C_{12}$-alkyl, which may be oxygen-interrupted, $C_5$-$C_6$-cycloalkyl or $C_7$-$C_{12}$-phenylalkyl where the phenyl is unsubstituted or monosubstituted, disubstituted or trisubstituted by $C_1$-$C_4$-alkyl, $C_1$-$C_4$-alkoxy, fluorine, chlorine or bromine, or

is a from 5- to 12-membered cycloaliphatic ring which may be monosubstituted, disubstituted, trisubstituted or tetrasubstituted by $C_1$-$C_4$-alkyl, and R$^3$ is hydrogen, $C_1$-$C_8$-alkyl, $C_2$-$C_3$-cyanoalkyl, $C_2$-$C_4$-hydroxyalkyl, $C_2$-$C_3$-aminoalkyl, $C_1$-$C_8$-alkanoyl or $C_7$-$C_{10}$-phenylalkyl where the phenyl is unsubstituted or monosubstituted or disubstituted by $C_1$-$C_4$-alkyl, $C_1$-$C_4$-alkoxy, fluorine, chlorine or bromine, or an acid addition salt or hydrate thereof.

2. A tetrahydropyridone as claimed in claim 1, wherein R$^1$ and R$^2$ are each $C_1$-$C_5$-alkyl.

3. A tetrahydropyridone as claimed in claim 1, wherein

is a from 5- to 12-membered cycloaliphatic ring.

4. A tetrahydropyridone as claimed in claim 1, wherein R$^3$ is hydrogen.

5. A tetrahydropyridone as claimed in claim 2, wherein R$^3$ is hydrogen.

6. A tetrahydropyridone as claimed in claim 3, wherein R$^3$ is hydrogen.

* * * * *